(12) United States Patent
Effing et al.

(10) Patent No.: US 9,029,625 B2
(45) Date of Patent: May 12, 2015

(54) FILM DRESSING WITH IMPROVED APPLICATION ASSISTANCE

(75) Inventors: Jochem Effing, Kelkheim-Fischbach (DE); Axel Eckstein, Heidenheim (DE)

(73) Assignee: Paul Hartmann AG (DE)

( * ) Notice: Subject to any disclaimer, the term of this patent is extended or adjusted under 35 U.S.C. 154(b) by 0 days.

(21) Appl. No.: 11/849,291

(22) Filed: Sep. 2, 2007

(65) Prior Publication Data

US 2008/0281246 A1 Nov. 13, 2008

Related U.S. Application Data

(63) Continuation of application No. PCT/EP2006/001741, filed on Feb. 24, 2006.

(30) Foreign Application Priority Data

Mar. 3, 2005 (DE) .......................... 10 2005 009 634

(51) Int. Cl.
*A61F 13/00* (2006.01)
*A61F 13/02* (2006.01)

(52) U.S. Cl.
CPC ..... *A61F 13/023* (2013.01); *A61F 2013/00182* (2013.01); *A61F 2013/00289* (2013.01); *A61F 2013/00412* (2013.01); *A61F 2013/00868* (2013.01)

(58) Field of Classification Search
USPC ......... 602/58, 57, 41, 42, 43, 54, 52; 604/386
See application file for complete search history.

(56) References Cited

U.S. PATENT DOCUMENTS

| | | | | |
|---|---|---|---|---|
| 4,753,232 A * | 6/1988 | Ward | .............................. | 602/52 |
| 4,832,008 A * | 5/1989 | Gilman | ........................... | 602/57 |
| 5,308,313 A * | 5/1994 | Karami et al. | ................... | 602/55 |
| 5,336,162 A * | 8/1994 | Ota et al. | ......................... | 602/41 |
| 5,628,724 A * | 5/1997 | DeBusk et al. | ................. | 602/58 |
| 5,733,251 A * | 3/1998 | Johns | .............................. | 602/57 |
| 5,960,795 A * | 10/1999 | Schultz | .......................... | 128/888 |
| 6,129,929 A * | 10/2000 | Wick | ............................. | 424/448 |
| 6,297,422 B1 * | 10/2001 | Hansen et al. | ................... | 602/57 |
| 7,723,561 B2 * | 5/2010 | Propp | ............................. | 602/58 |
| 2008/0171958 A1 * | 7/2008 | Gundersen | ....................... | 602/56 |

FOREIGN PATENT DOCUMENTS

| | | | |
|---|---|---|---|
| EP | 0401949 A2 * | 5/1990 | |
| EP | 0401949 A2 * | 5/1990 | |
| JP | 03-007153 | 6/1989 | |
| JP | 07-38138 | 12/1993 | |

* cited by examiner

*Primary Examiner* — Victoria J Hicks
(74) *Attorney, Agent, or Firm* — Brinks Gilson & Lione

(57) ABSTRACT

A film structure having a polymer film and an application system enabling the film structure to be handled in a simple manner. The application system is arranged on a first side of the polymer film and has at least one supporting film to which at least one gripping strip is applied. The polymer film also has at least one first region without a supporting film.

17 Claims, 5 Drawing Sheets

FILM DRESSING WITH IMPROVED APPLICATION ASSISTANCE

CROSS-REFERENCE TO RELATED APPLICATIONS

This application is a continuation of International Application No. PCT/EP2006/001741 filed on Feb. 24, 2006, which claims the benefit of German Patent Application No. 10 2005 009 634.4, filed Mar. 3, 2005. The disclosures of the above applications are incorporated herein by reference.

FIELD

The present disclosure relates to film dressings and in particular application systems for film dressings.

BACKGROUND

The statements in this section merely provide background information related to the present disclosure and may not constitute prior art.

Application aids for adhesive bandages or wound dressings have been known for quite some time. These application aids are particularly used for film dressings. Film dressings are thin, usually transparent, semipermeable films or foils made of polymer materials. The semipermeable nature of the films prevents the penetration of bacteria or moisture and thereby guarantees a sufficient exchange of oxygen and condensation between the skin to be covered and the outside surroundings of the film dressing. These film dressings are used in a variety of ways—for example, as an incision film for sterile covering of surgery wounds, as a water-proof cover of wound dressings that absorb exudates, and for positioning catheters or cannulas. Due to the minimal thickness of these films and their respective instability, these film dressings are equipped with a wide variety of application aids. Most of these application aids use an additional supporting layer which is removed during or after the application of the film dressing.

The patent literature has also known film wound dressings for quite some time. For example, EP 81 990 B1 describes an adhesive wound dressing that consists of a thin polymer film. This polymer film is coated on one side with an adhesive material that adheres to the skin, which in turn is covered with a removable layer. On the other side, which during application is opposite of the body, the polymer film also has an easily removable support layer to improve the ease of use, which consists of a fibrous material, for example, a non-transparent non-woven material. This support layer is of the same size as the polymer film.

EP 690 706 B1 describes an adhesive wound dressing, which has a carrying layer to aid the ease of application of a polymer film, which is comprised by a wound dressing. This carrying layer completely covers the polymer film and can be removed from the polymer film in two steps. For this purpose, a center section is removed from the carrying layer, whereas in the next step a frame section is removed. The fact that it is difficult for the user to grasp the carrying layer of this wound dressing is unfavorable.

In addition, EP 951 263 B1 describes an adhesive film dressing, the adhesive side of which at least one two-part removable protective layer covers the adhesive side and where its non-adhesive second side comprises a one-part support layer. The support layer in this film dressing is hinge-like attached to the protective layer on two opposite sides so that the support layer is removed simultaneously with the support layer.

EP 473 918 B1 describes a film dressing that comprises a one-sided supporting film, which in turn has one grip strip on each of the two opposite sides. This position of the grip strips has the disadvantage that there is no pre-determined direction for removing the supporting film.

EP 985 931 A1 describes a film-based dressing material, which comprises a non-adhesive gripper in the peripheral area of the film. The non-adhesive side of the film comprises a one-part support layer, which is equal to the size of the film and comprises at least one grip strip. By pulling the gripper in the direction of the adhesion, the applied film can be removed again painlessly.

The European patent specification EP 630 628 B1 established a film dressing that comprises for the ease of application a two-part supporting film. This supporting film is larger than the film to be applied and completely covers it. In order to remove the supporting film, the supporting film comprises an additional adhesive removal strip, which is positioned above the intersection line of the supporting film and for handling purposes has two non-adhesive peripheral areas that serve as grip strips. This additional removal strip serves to remove only a portion of the supporting film, whereas the second part of the supporting film remains on the polymer films.

WO 97/25012 A1 suggests a film dressing which is provided either continuously or only on two opposing peripheral areas of the film with a two-part supporting layer. If the supporting film is continuously attached to the film dressing, then gripper supports may be positioned on the supporting film. The adhesive protective layer opposite of the supporting layer is divided into three sections.

These industrial property rights present various alternative solutions to film and foil dressings with various application systems. The film dressings which have been suggested as a solution in these industrial property rights are viewed in part as too complicated in their construction and too complicated in their application. Furthermore, the film dressings with application aids suggested in these protective rights all exhibit a rigidity which is considered too high in respect of the very flexible polymer film that is actually to be applied. This flexibility of the film dressings is necessary, however, to apply the polymer films which are actually to be applied, accurate and wrinkle-free.

SUMMARY

The present disclosure presents a film dressing with application system, which has a simple structure and yet assures wrinkle-free application of the polymer film. At the same time, it is possible to apply the film dressing universally without any limitation to shape or size.

Accordingly, a film dressing is provided that comprises a polymer film and an application system for permitting an improved ease of use of said film dressing, where the application system is located on the first side of the polymer film and comprises at least one first and one second supporting film, where at least one grip strip is molded, whereby the polymer film comprises at least one first supporting film-free area and the grip strip at least partially overlaps the first supporting film-free area.

An advantage of such a film dressing with an application system lies in the fact that the supporting film-free area of the polymer film, that is, the area which is not covered by a supporting film, can function as a joint during the application of the film dressing, thanks to the greater flexibility thereof, by comparison to the polymer film with the supporting film. This being the case, even a relatively rigid support material can be used as a supporting film, plus at the same time guaranteeing a snug-fitting application. On the other hand, in the state of the art, whether a supporting film in one part which is of the same size as the polymer film, or a supporting film in several parts which, as a whole, is of the same size as the polymer film, is used, the choice of the support material must be limited to relatively flexible materials, in order to guarantee a snug-fitting application of the polymer film. A further advantage lies in the saving on the material used for the supporting film.

Furthermore, the fact that at least one section of the supporting film-free area is covered by the grip strip reduces the risk of contamination or damage to the polymer film.

The "Application system" according to the present disclosure shall include everything that permits the improved ease of use of the polymer film and comprises at least two supporting films and in addition to these supporting films comprises at least two grip strips, which are molded to said supporting films. "Molding" in this context shall mean the combining of two similar or two different materials, which are separable or inseparable from one another by means of adhesives, pressure, thermal energy, ultra-sonic applications or other procedures. The grip strip is therefore presently always an additional material component, whereas the grip strip can always be removed from the polymer film with at least one supporting film. Furthermore, for the ease of understanding in the context of the present disclosure, a film or polymer film shall always refer to the film or polymer film actually to be applied, for example a wound dressing; in contrast, a film or polymer and/or supporting film shall always refer to a part of the application system, that means the difference between film and foil in this case only refers to the function of the components. No distinction shall be made in respect of the material between the terms of film and foil.

Because of the first supporting film-free area, the surface of the polymer film which is covered by supporting film is accordingly smaller than the surface of the first side of the polymer film. The film dressing comprises in particular one or more supporting films, whereby the total contact surface of said supporting films is less than about 97%, and especially less than about 94%, of the area of the first side of the polymer film to be applied.

An additional embodiment of the disclosure provides for a grip strip which completely overlaps an area of the polymer film which is not covered by supporting films. In this case, the application system in its entirety can be of the same size as the polymer film. The reference to "the same size" indicates the size of the contact area; that is, the limitation of the perimeter of the application system and that of the polymer film are aligned. The fact that the application system and the polymer film are the same size, and the fact that the grip strip is merely molded to the supporting film and is not connected to the polymer film, guarantee that, in addition to the previously described high level of flexibility in the area which is not covered by the supporting film, the entire film is covered, and is therefore also completely protected before and during the application.

In a first preferred embodiment of a film dressing according to the present disclosure, the first grip strip comprises a grip area that can be determined by the user when grasping said grip strip, preferably designed as a rear grip device of at least about 2 $cm^2$, particularly at least about 5 $cm^2$ and especially preferred of at least about 7 $^2$.

In particular, a first area that is not covered by the supporting films can be positioned at the edge of the polymer film. An edge shall be understood as every section of an area, which extends from the border of an area into the interior of an area, whereas the area extension of the edge is smaller than about 50% of the entire area. This provides a film dressing which favorably comprises an area, which comprises a flexibility that is pre-determined by the polymer film itself and assures an easy first positioning of the film to be applied, where at the same time the supporting films assure secure handling in the additional areas. It has been proven that it is particularly easy and safe to manipulate when one of the supporting films has in at least one point of its outer edge a distance from the outer edge of the polymer film of at least about 2 mm, particularly at least about 3 mm and especially of at least about 5 mm. Particularly preferred is a distance which has in each point of the edge of the supporting film an equal distance of at least about 2 mm, particularly at least about 3 mm and especially at least about 5 mm to the outmost edge of the polymer film.

In a further embodiment of this disclosure, the application system includes two supporting films which are applied on a plane parallel to the polymer film. In such an embodiment of this disclosure, a first supporting film-free area may be located between the first and the second supporting films. The distance between both supporting films is preferably in each point at least 2 mm, particularly about 3 mm and especially about 5 mm. Particularly preferred is an application system that has two supporting films, which in each point have the same distance to one another.

The embodiment of the film dressing with two supporting films especially provides for each of the supporting films to include one grip strip. Accordingly, a first grip strip is arranged on the first supporting film and a second grip strip is arranged on the second supporting film.

A preferred embodiment of this film dressing according to the disclosure with two supporting films provides for the first grip strip to exhibit a gripping surface designed to be gripped by the user, preferably implemented as a means of gripping from behind, and for the first grip strip with this gripping surface to protrude over at least one section, and especially over all, of the second grip strip.

This positioning of the grip strips provides the user with a particularly simple means to manipulate in each case only the upper-most first grip strip as the first grip strip and therefore remove a first supporting film as the first film from the polymer film. The user is only able to remove a second supporting film in the second step with the aid of a second grip strip. This determines a succession in the removal of the supporting films and provides a particularly safe means of handling the film dressing.

The size of the gripping surface of the first grip strip is preferably at least about 2 $cm^2$, particularly at least about 5 $cm^2$ and especially preferred of at least about 7 $cm^2$. It is particularly intended that the first grip strip completely overlap the second grip strip. It has been proven particularly safe to manipulate when the first grip strip comprises an exposed grip area of at least about 2 $cm^2$, particularly at least about 4 $cm^2$ and especially preferred of at least about 6 $cm^2$. This exposed grip area is in this case the section of the grip area that marginally protrudes the second grip strip.

It has been shown to be especially easy to handle when the first grip strip protrudes completely over both the supporting film-free area of the polymer film and the second grip strip.

If the film dressing comprises an application system with two supporting films and a first area without supporting film is intended between the supporting films, separate from this first non-covered area a second area can be designed, which is also not covered by a supporting film. This second area can furthermore preferably be covered by a grip strip. Another design is also possible where this second area is covered neither by a supporting film nor by a grip strip. In the preferred version, this second non-covered area of the polymer film is positioned at one edge of the film dressing. The film dressing in this manner comprises a joint within the dressing as well as an area for its initial positioning.

If an application system is intended that comprises more than two supporting films, then each supporting film can be assigned to a grip strip. In a particularly preferred embodiment, two supporting films may be assigned to one grip strip. In particular, in one film dressing with three supporting films, two supporting films can be assigned to one grip strip. With this arrangement and/or assignment of the grip strips on the supporting films, two separate supporting films can be removed in one-step.

Transparent or translucent film materials are particularly intended as supporting films. However, opaque or non-transparent film materials can be used alternatively. Used as supporting film are particularly those films that are manufactured from polyester, polyethylene, polypropylene, polyvinylchloride, polystyrene, polyamide, polycarbonate, cellulose ester, ethylene vinyl acetate, polyvinyl acetate, polyvinyl alcohol and/or combinations thereof. Particularly preferred are supporting films from transparent polyester or polyethylene or polypropylene. At the same time, it has been proven to be particularly preferable when the thickness of the supporting films are adjusted to comprise a thickness of about 15 to about 80 µm, particularly of about 20 to about 60 µm and especially of about 20 to about 40 µm.

In order to manufacture a grip strip, the same materials can be used that are used for the supporting films. In a particularly preferred embodiment, the grip strip is manufactured from a film material that is more flexible than the supporting film. If an application system is intended that comprises two or more supporting films and two or more grip strips, then all grip strips are manufactured from one material that is more flexible than any supporting film. This assures that the grip strips are very easy to grasp. In another particularly preferred embodiment with two grip strips, it is intended that the grip strip of the first supporting film is more flexible than the grip strip of the second supporting film. At the same time, it is also advantageous if the second grip strip completely overlaps the first grip strip.

An activation device can be provided in addition to a system with two grip strips that is positioned between the first and the second grip strip. This activation device can for example be an additional adhesive strip with an adhesive strength that is different for the contact surface of each side. When using such film dressings, one first grip strip, which is positioned above the second grip strip, can for example be grasped and with this grip strip the activation device and one supporting film can be removed from the polymer film, whereas the second grip strip is hence simultaneously activated and/or lifted up in such manner that it is easier for the user to grasp.

Alternatively, in a further embodiment of the film dressing, it is also possible for only a perimeter area of the polymer film to be at least partially covered by at least one supporting film, whereby a supporting film-free central area remains within the perimeter area of the polymer film. In this configuration, the supporting film is provided as a kind of frame, which gives the film dressing the necessary stability and safety in order to ensure a full-free application and, irrespective of the material used for the supporting film, simultaneously enables a precise aim at the place where the film dressing is to be applied. Accordingly, in this configuration, it is possible to use not only transparent or translucent supporting films, but also opaque or non-transparent ones as well. The grip strip attached to the supporting film should preferably be made of a transparent or translucent material.

In a film dressing according to the present disclosure, polymer films can be particularly used that are highly permeable to condensation. For this, those films are particularly practical that are manufactured from polyurethane, polyether urethane, polyester urethane, polyether-polyamide urethane, polyacrylate or polymethacrylate. Particularly preferred as polymer film is a polyurethane film, polyester urethane film or polyether urethane film. Most particularly preferred are also such polymer films that have a thickness of 15 to 50 µm, particularly of 20 to 40 µm and especially of 25 to 30 µm. The condensation permeability of the polymer film in a film dressing according to the present disclosure is preferably at least about 750 $g/m^2/24$ hrs., particularly at least about 1000 $g/m^2/24$ hrs., and especially at least about 2000 $g/m^2/24$ hrs. (measured according to DIN 13726).

An adhesive can be applied on the second side, which is opposite of the application system, of the polymer film to be applied. This application can be continuously as well as discontinuously or only in certain areas. The applied adhesive can be a common adhesive, particularly an acryl adhesive or a pressure-sensitive adhesive on polyurethane basis. Preferred are gel adhesives, especially on polyurethane basis, particularly water-based polyurethanes. Especially preferred are hydro-gel adhesives, particularly on water-based acrylics.

In the preferred version, the basic weight of the adhesive is about 20-about 100 $g/m^2$, particularly about 35-about 50 $g/m^2$, whereas the adhesive can be applied discontinuously, but preferably continuously.

The condensation permeability of the polymer film which has been prepared with adhesive is preferably at least about 1000 $g/m^2/24$ hrs, particularly preferred about 1200 $g/m^2/24$ hrs, and especially preferred at least about 2000 $g/m^2/24$ hrs. (measured according to DIN EN 13726).

According to a development of the present disclosure, the film dressing on the second side of the polymer film opposite of the application system can be continuously coated with an adhesive and the adhesive be protected with a cover paper. Any commonly available silicone paper or film as well as a paper or film coated with a fluoride combination can be used as a cover layer.

If the film dressing is to be produced as a wound dressing, according to a further embodiment a wound pad or wound cushion must be positioned on the second side of the polymer film, which during the application is positioned towards the body. Such film dressing is particularly suited as wound cover when the wound pad or cushion is adhesively attached to the polymer film. This wound cushion can be made of fleece, therefore a non-woven material. This fleece is preferably a hydrophilic fibrous material such as cotton, viscose, cellulose and polyester or their combinations, preferably with hydrophilic polyethylene or polypropylene.

Instead of the wound cushion or in addition to the wound cushion, the film dressing can on the second side of the polymer film, which during the application is positioned towards the body, particularly be provided with a layer that promotes the healing of the wound. A layer that promotes the healing of the wound means any layer that is used for treatment on moist wounds. Particularly preferred here are hydrogels based on polyurethane, acrylics or water-soluble celluloses or combinations thereof, which comprise water content of at least 20%, preferably at least 50% in relation to the total weight of the hydrogel. These hydrogels can be applied directly to the wound cushion as well as to the second side of the polymer film.

In order to provide a film dressing that is safe to handle, the used materials must be precisely in coordination with one another. The used materials must be particularly coordinated in respect of their release characteristics. These release characteristics that are adjustable with additional means are based on the forces that exist between the two used materials. A targeted surface treatment of a material can for instance be used to adjust an attracting of rejecting effect in relation to a second material, which is to be joined with the first material. A surface treatment, which causes an attracting effect between two materials, can for instance follow due to an adhesive coating, a static charge or by amalgamating both materials that are to be joined. A rejecting effect can for instance be caused by an additional layer on a material of silicon or fluoride combinations. A release force (pull-off force) is thereby such a force that is necessary to separate two materials from one another (measured according to DIN 53530).

In another embodiment of the film dressing according to the present disclosure, these release characteristics are adjusted in such manner that the pull-off force which is necessary to release a cover film or paper from the polymer film to be applied is greater than the pull-off force which is necessary to release the supporting film or the supporting foils from the polymer film.

In a development of the film dressing with two supporting films the release characteristics are adjusted in such manner that the pull-off force which is necessary to release the first supporting film from the polymer film that is to be applied is equal to the pull-off force that is necessary to release the second supporting film.

In a film dressing with two supporting films and two grip strips the release characteristics are preferably adjusted in such manner that the pull-off force which is necessary to release the first grip strip from the second grip strip or to release the second from the first grip strip is less than the pull-off force that is necessary to release the supporting film from the polymer film that is to be applied.

In another development of the film dressing with two supporting films the release characteristics are preferably adjusted in such manner that the pull-off force which is necessary to release the first supporting film from the polymer film that is to be applied is greater than the pull-off force which is necessary to release the first grip strip from the second grip strip.

The adhesion of the supporting film on the polymer film is preferably only about 0.01 to about 0.5 N/25 mm, especially preferred about 0.01 to about 0.1 N/25 mm, measured according to DIN 53530. The supporting material is preferably attached directly here to the polymer film during its manufacturing process, or the polymer film is manufactured directly on the supporting material, respectively. Further, all regular methods for the film manufacturing may be applied, such as melting, spreading, extrusion or other familiar methods for manufacturing of films or foils. If necessary, the supporting material can be roughened on the coated side or be subjected to another treatment that promotes adhesion. A coating that promotes adhesion can also be beneficial.

In a particular development of the present disclosure, it is intended that a film dressing including a polymer film with an application system is located inside of a package. It is particularly intended that the package is a sterile package.

It must be emphasized at this point that the here referenced characteristics of the alternative developments of the present disclosure are not to be limited to the individual alternatives. It is rather the case that the combination of the developments and/or the combination of the individual characteristics of the alternative forms must be included in a development according to the present disclosure. The present disclosure shall be understood to be reduced just as little by the subsequent explanations of the illustrations.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

The invention is described in greater detail below by means of the drawings, which show:

FIG. 1 is a top view of a first embodiment of a film dressing constructed in accordance with the principles of the present disclosure;

FIG. 2 a top view of a second embodiment of a film dressing constructed in accordance with the principles of the present disclosure;

DETAILED DESCRIPTION

The following description is merely exemplary in nature and is not intended to limit the present disclosure, application, or uses.

Figure 1:
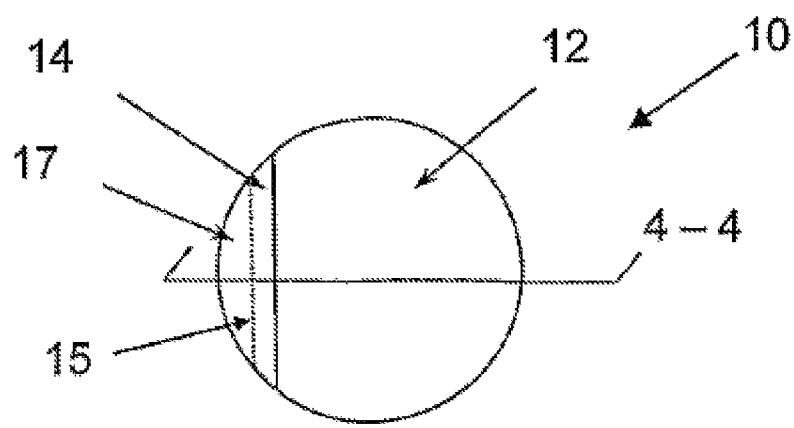
Figure 4:
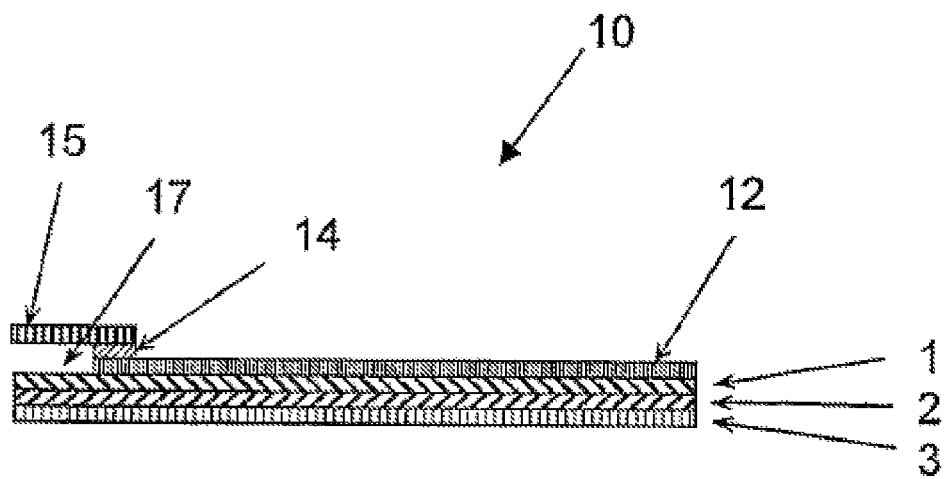
FIG. 4 is a cross-sectional view, taken along line 4-4 of FIG. 1, of a film dressing in accordance with the principles of the present disclosure.

FIGS. 1 and 4 show a first embodiment of a film dressing according to the disclosure. The film dressing (10) is shown in a round shape. It consists of a transparent polymer film (1) which is covered, on the first side thereof, with an application system. Applied on the second side, the side opposite of the application system, is an adhesive (2) which is covered by a cover layer (3). The application system consists of a similarly transparent supporting film (12), which covers one part of the polymer film, a grip strip (15) and an adhesive (14). In a margin segment (17), the polymer film is supporting film-free. The grip strip (15) is molded to the supporting film (12) by means of the adhesive (14). This grip strip fully overhangs the supporting film-free area (17) of the polymer film. The grip strip is not connected in any way to the polymer film, so that, when the film is in use, the grip strip can be gripped at once without effort. The polymer film is completely covered by the application system, whereby, at the same time, the supporting film-free area (17) creates a flexible area which, when the film dressing is applied, can primarily be used for initial attachment.

Figure 2:
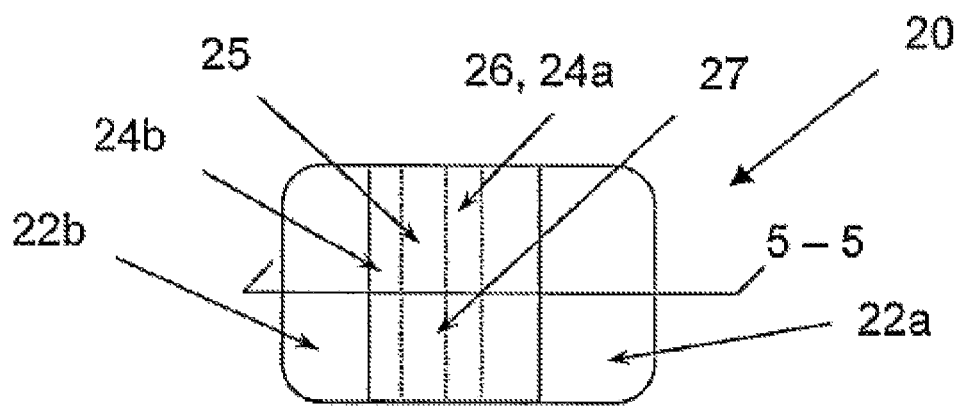
Figure 5:
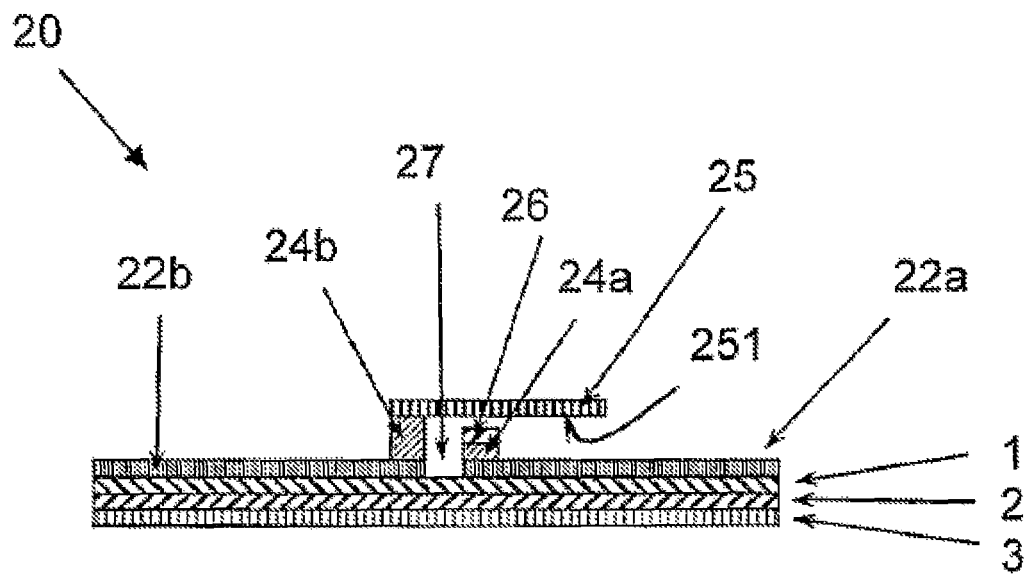
FIG. 5 is a cross-sectional view, taken along line 5-5 of FIG. 2, of a film dressing in accordance with the principles of the present disclosure.

FIGS. 2 and 5 show a second embodiment of a film dressing according to the disclosure. This film dressing (20) is basically rectangular in shape and, similarly to the first embodiment, consists of a polymer film (1), an adhesive layer (2) which is applied to the entire surface of the polymer film, and a cover layer (3) which covers the adhesive layer. The polymer film, on the first side thereof, exhibits an application system, which consists of two supporting films (22a, 22b), two grip strips (25, 26) and two adhesives (24a, 24b). The two grip strips are applied to the polymer film in such a way that the polymer film is completely covered by the supporting films, up to a supporting film-free area (27). The covered area of the polymer film amounts to approximately 96% of the surface of the first side of the polymer film. In this embodiment, the first grip strip (25), which is glued to the first supporting film (22b) by means of the first adhesive (24b), overhangs both the supporting film-free area (27) and the second grip strip (26), which is glued to the second supporting film (22a) by means of the second adhesive (24a). The first grip strip (25) exhibits a gripping surface which is meant to be gripped from behind by the user. The outer part of the gripping surface protrudes laterally as a free gripping surface (251) over the second grip strip (26). This second grip strip (26), in the embodiment represented, does not exhibit a gripping surface which is meant to be gripped from behind. This possibility, however, is just as conceivable as the one shown in FIGS. 3 and 6 for a cannula plaster, and is advantageous in order to facilitate the gripping of the second grip strip (26). The fact that only one grip strip can be gripped and is visible to the user guarantees a sequence of actions in the removal of the two supporting films.

Figure 3:
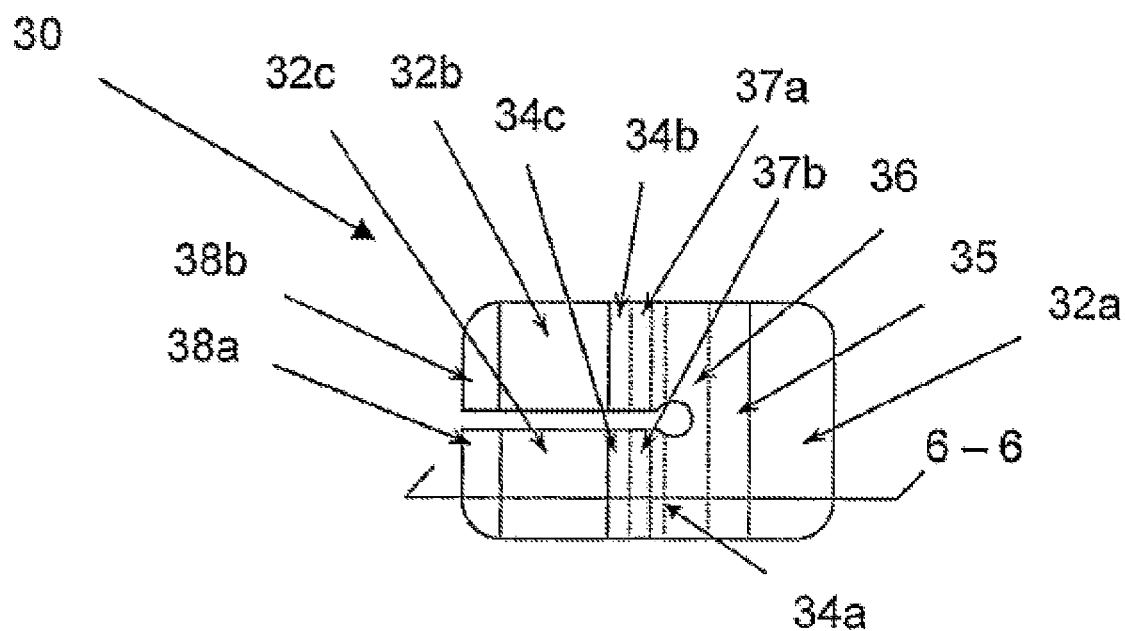
FIG. 3 is a top view of a third embodiment of a film dressing constructed in accordance with the principles of the present disclosure.
Figure 6:
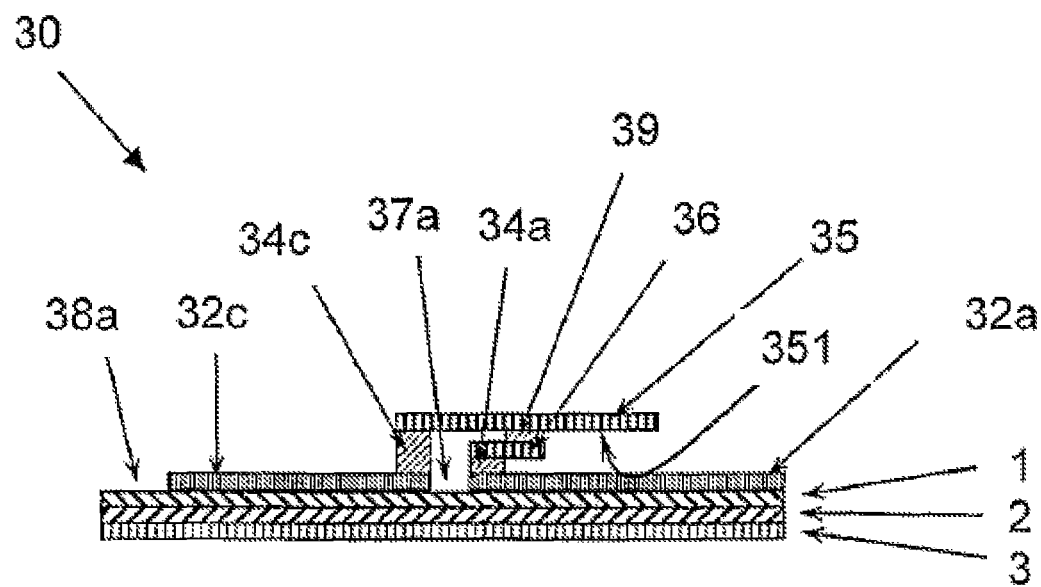
FIG. 6 is a cross-sectional view, taken along line 6-6 of FIG. 3, of a film dressing in accordance with the principles of the present disclosure.

FIGS. 3 and 6 show a further film dressing (30). This film dressing can be used as a cannula or catheter plaster. The film dressing exhibits a basically rectangular shape, the short side whereof exhibits a recess parallel to the long side. By means of this recess, the film dressing is given two mutually independent areas, which are connected to each other by means of a third area, and each of which, in the attachment, for example, of a cannula, can be attached to a surface on either side of the cannula. The film dressing exhibits a polymer film (1), an acrylate adhesive layer (2) and a cover layer (3) which covers the adhesive layer. Arranged on the first side of the polymer film, which faces away from the adhesive layer, is an application system. This application system includes two grip strips (35, 36), which are attached to three supporting films (32a, 32b, 32c) by means of three adhesives (34a, 34b, 34c). The first grip strip (35) is provided for both the first supporting film (32c) and the second supporting film (32b) and is accordingly molded to both of them. This means that both of these supporting films (32c, 32b) can be removed by means of a single grip. The first grip strip (35) overhangs both the central areas of the polymer film, which are not covered by supporting films (37a, 37b) and the second grip strip (36). The outer part of the gripping surface protrudes laterally as a free gripping surface (351) over the second grip strip (36), so that, here too, a series of actions is guaranteed in the removal thereof.

The supporting films, taken together, cover a surface of the polymer film which accounts for about 92% of the surface of the first side of the polymer film. This is because, in addition to the central areas, which are not covered by supporting films (37a, 37b), there is also no supporting film on the two margin segments (38a, 38b). These margin segments, after the cover layer has been removed, can be used for initial attachment. To this end, FIG. 6 shows a means of activation (39) between the two grip strips. This means of activation (39), similarly to the adhesive used to fasten the grip strip (36) on to the supporting film (32a), is not shown in FIG. 3. This means of activation (39) is a double-sided adhesive tape, which shows a higher adhesive forced to the first grip strip (35) had to the second grip strip (36). Accordingly, when the supporting films (32b, 32c) are removed, the first grip strip (35) causes the second grip strip (36), which lies beneath it, to stand upright, before the adhesive forced between the first grip strip (35) and the means of activation (39) is removed. The second grip strip (36) thus becomes easier to grip in the second stage, in order to remove the second supporting film (32a).

Figure 7A:
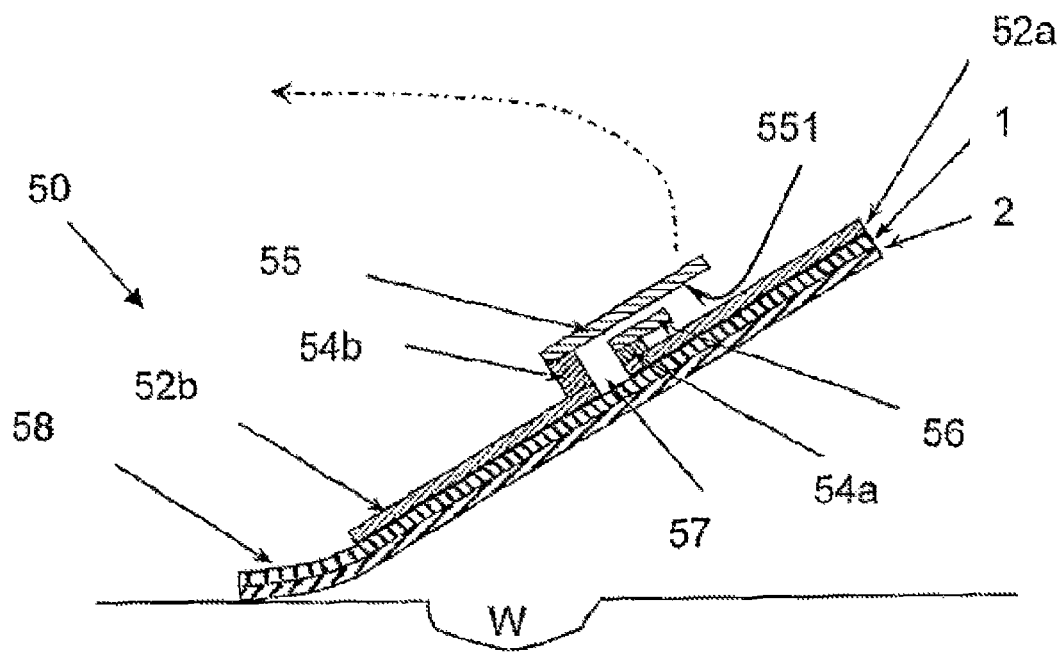
FIGS. 7 a-c are cross-sectional views of a film dressing in use in accordance with the principles of the present disclosure.
Figure 7B:
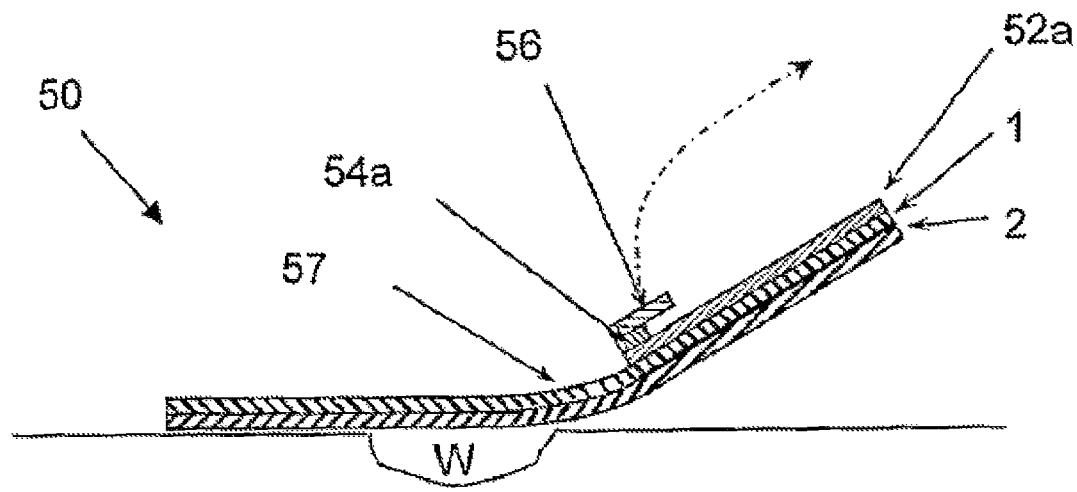
Figure 7C:
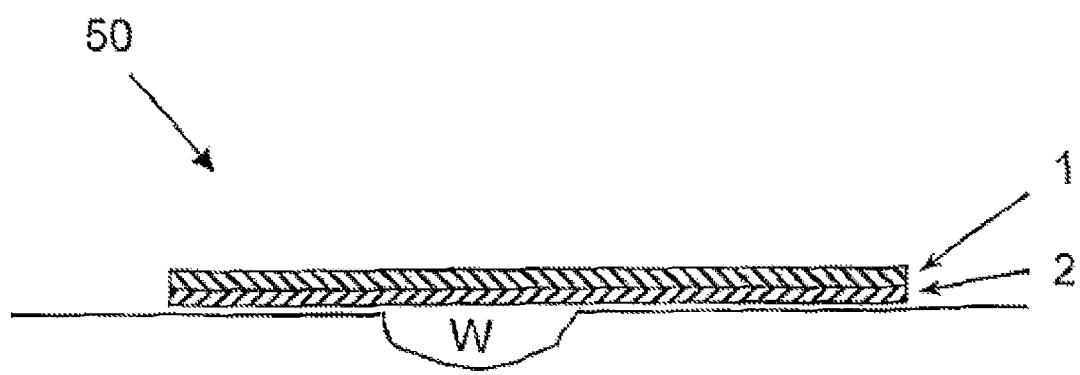

In the use of a film dressing according to the disclosure (10, 20, 30, 50), the removal of the cover layer (3) from the adhesive layer (2) is first provided. As shown in FIGS. 7a through 7c, in the case of a film dressing with two supporting film-free areas, in order to apply such a film dressing (30, 50), for example, above a wound (W), it is possible to attach a first supporting film-free margin segment (38a, 38b, 58) to an area which adjoins the wound (W). Thanks to the high degree of flexibility of the polymer film in the supporting film-free area, this is quite possible. In the next step, the user, by making use of the arrangement of the grip strips (35, 36, 55, 56), which are attached to the respective supporting films by means of adhesive gluing means (34a, 34b, 34c, 54a, 54b), can place the polymer film to be applied (1) precisely the wound. By means of the second supporting film-free margin segment (37a, 37b, 57), the film dressing exhibits a kind of joint which guarantees a full-free application. The supporting films (32a, 32b, 32c, 52a, 52b) can be removed one after the other during the application, or can be removed one after the other following the successful application, of the polymer film. In so doing, the first grip strip (35, 55) is first gripped, by means of its free gripping surface (351, 551), in order to be able to remove the first supporting film (32b, 32c, 52b) first.

Embodiment 1:

The film dressing comprises a rectangular basic form with an edge length of about 57×about 80 mm (contact surface about 45.6 cm$^2$). It comprises a transparent polyether urethane film, which on the side that is positioned towards the body is coated with an acrylate-based hydrogel adhesive. The adhesive is affixed continuously in the amount of about 35 g/m$^2$ onto the about 25 µm thick polymer film (measured with a test pressure of about 0.5 kPa). The polymer film together with the adhesive comprises a condensation permeability of about 2,600 g/m$^2$/24 hrs. (measured according to DIN EN 13726, with the difference that after about 4 hrs. the measurement period was terminated and the determined result is extrapolated for about 24 hrs.). Such a polymer film is available under the trade name Inspire 6200 from the company InteliCoat Technologies, Wrexham Industrial Estate, Wrexham LL13 9UF, UK. The adhesive side of this polymer film is available from the company Maria Soell GmbH & Co. KG, Frankenstrasse 45, D-63667 Nidda-Eichelsdorf, with a siliconized cover paper and covered under the trade name Separacon 980-60. The other side of the polymer film, which during the application is positioned away from the body, comprises an application system, which consists of two supporting films that each has one grip strip. The supporting films are as illustrated in FIG. 1 and FIG. 2 positioned on the polymer film. The film dressing at hand additionally realizes a peripheral area, which is not covered by a supporting film or grip strip. This additional peripheral area without a supporting film is positioned on the short side of the rectangle and comprises an equal width of about 5 mm. Both of the supporting films are equal in size and comprise an edge length of about 57×about 36 mm (contact area: 2×20.5 cm$^2$=about 41.0 cm$^2$). The distance of both films is about 3 mm in each point of their parallel edges that are of equal length. This results for both supporting films in a combined contact area of about 90% in respect of the surface of the first polymer film. The supporting films are manufactured of a 30 µm thick polyester film (measured at a test pressure of about 0.5 kPa). A grip strip is affixed onto each supporting film with an acrylate adhesive. The grip strips together comprise a configuration, as illustrated in FIG. 4, whereas the first grip strip, which is sketched with reference mark (35), has a size of about 57×about 39 mm and is throughout the entire width (about 57 mm) attached to the respective supporting film. The second grip strip, which is illustrated with reference (36), comprises a size of about 57×about 22 mm. Both grip strips are each attached to the respective supporting film through an about 5 mm wide adhesive connective strip and are manufactured from a 20 µm thick transparent polyester film. The first grip strip thus has a strip surface with an equally formed width of about 34 mm. The size of the grip surface of the first grip strip comprises about 19.4 cm². The equally shaped width of the grip surface of the second grip strip comprises about 17 mm. The size of the grip surface of the second grip strip thus comprises about 9.7 cm². The equally shaped width of that portion, which protrudes beyond the second grip strip, of the first grip surface that is the width of the exposed grip surface of the first grip strip measures about 9 mm. The size of the exposed grip surface thus comprises about 5.1 cm².

Embodiment 2:

The film dressing comprises a rectangular basic form with an edge length of about 57×about 80 mm (contact surface about 45.6 cm²). It comprises a transparent polyether urethane film, which on the side that is positioned towards the body is coated with a pressure sensitive acrylate-based adhesive. The adhesive is affixed continuously in the amount of approx. 25 g/m2 onto the approx. 30 µm thick polymer film (measured with a test pressure of about 0.5 kPa). The polymer film together with the adhesive comprises a condensation permeability of about 1,200 g/m²/24 hrs. (measured according to DIN EN 13726). Such a polymer film is available under the trade name Inspire 1305 from the company InteliCoat Technologies, Wrexham Industrial Estate, Wrexham LL13 9UF, UK. The adhesive side of this polymer film is available from the company Maria Soell GmbH & Co. KG, Frankenstrasse 45, D-63667 Nidda-Eichelsdorf, with a siliconized cover paper and covered under the trade name Separacon 980-60. The other side of the polymer film, which during the application is positioned away from the body, comprises an application system, which consists of two supporting films that each has one grip strip. The supporting films are as illustrated in FIG. 1 and FIG. 2 positioned on the polymer film. The film dressing at hand additionally realizes a peripheral area, which is not covered by a supporting film or grip strip. This additional peripheral area without a supporting film is positioned on the short side of the rectangle and comprises an equal width of about 5 mm. Both of the supporting films are equal in size and comprise an edge length of about 57×about 36 mm (contact area: 2×20.5 cm²=about 41.0 cm²). The distance of both films is about 3 mm in each point of their parallel edges that are of equal length. This results for both supporting films in a combined contact area of about 90% in respect of the surface of the first polymer film. The supporting films are manufactured of a 30 µm thick polyester film (measured at a test pressure of about 0.5 kPa). A grip strip is affixed onto each supporting film with an acrylate adhesive. The grip strips in a cross-sectional view comprise a configuration, as illustrated in FIG. 4, whereas the first grip strip, which is sketched with reference mark (35), has a size of about 57×about 39 mm and is throughout the entire width (about 57 mm) attached to the respective supporting film. The second grip strip, which is illustrated with reference mark (36), comprises a size of about 57×about 22 mm. Both grip strips are each attached to the respective supporting film through an about 5 mm wide adhesive connective strip and are manufactured from a 20 µm thick transparent polyester film. The first grip strip thus has a strip surface with an equally formed width of about 34 mm. The size of the grip surface of the first grip strip comprises about 19.4 cm². The equally shaped width of the grip surface of the second grip strip comprises about 17 mm. The size of the grip surface of the second grip strip thus comprises about 9.7 cm². The equally shaped width of that portion, which protrudes beyond the second grip strip, of the first grip surface, that is the width of the exposed grip surface of the first grip strip measures about 9 mm. The size of the exposed grip surface thus comprises about 5.1 cm².

The release characteristics of the materials used in this embodiment 2 were determined on about 60×about 80 mm test sections according to the method described in DIN 53 530. The tests were completed with a pull-off velocity of about 300 mm/min. The silicon paper in respect of the polymer film therefore exhibits a release force of about 0.77 N/25 mm, whereas the supporting film in respect of the polymer film exhibits a release force of about 0.09 N/25 mm. The release characteristics of this film dressing are hence adjusted such that the pull-off force which is necessary to release a cover film from the polymer film that is to be applied is greater than the pull-off force which is necessary to separate the supporting film or the supporting films from the polymer film.

It should be noted that the disclosure is not limited to the embodiment described and illustrated as examples. A large variety of modifications have been described and more are part of the knowledge of the person skilled in the art. These and further modifications as well as any replacement by technical equivalents may be added to the description and figures, without leaving the scope of the protection of the disclosure and of the present patent.

What is claimed is:

1. A film dressing including a polymer film and an application system for easier handling of the film dressing, whereby the application system is arranged on and within a surface area of a first side of the polymer film and includes two supporting films that are directly disposed on to the first side of the polymer film and are offset from one another and do not overlap, each of which has at least one grip strip whereby each of the at least one grip strip is affixed to the respective supporting film by an adhesive whereas each of the at least one grip strip is not directly adhered to the polymer film and can always be removed from the polymer film with the supporting film, and at least one supporting film-free area is between the offset supporting films in which the polymer film is not covered by the supporting films, and the at least one grip strip affixed to the respective supporting film protrudes above at least one section of the at least one supporting film-free area, wherein the two supporting films together cover less than 94% of the surface area of the first side of the polymer film.

2. The film dressing of claim 1, wherein the polymer film exhibits at least one second supporting film-free area, which is arranged separately from the at least one supporting film-free area.

3. The film dressing of claim 2, wherein the at least one second supporting film-free area forms a margin segment of the polymer film or is arranged between the two supporting films.

4. The film dressing of claim 1, wherein one of the at least one grip strip protrudes over at least a section of another of the at least one grip strip.

5. The film dressing of claim 4, wherein one of the at least one grip strip protrudes over the entirety of another of the at least one grip strip.

6. The film dressing of claim 1, wherein a second side of the polymer film is coated with an adhesive, and the adhesive coating the second side of the polymer film is covered with a cover sheet or cover paper.

7. The film dressing of claim 6, wherein the adhesive coating the second side of the polymer film covers an entire surface of the second side of the polymer film.

8. The film dressing according to claim 1, wherein the polymer film defines a recess adjacent to at least one of the two supporting films.

9. The film dressing according to claim 1, wherein the application system further comprises a third supporting film directly disposed on to the first side of the polymer film and having a grip strip affixed thereto by an adhesive.

10. The film dressing of claim 1, wherein at least one of the at least one grip strip protrudes entirely above the at least one supporting film-free area.

11. The film dressing of claim 1, wherein the at least one supporting film-free area is arranged between the two supporting films.

12. The film dressing of claim 1, wherein the at least one supporting film-free area forms a margin segment of the polymer film.

13. The film dressing of claim 1, whereby each of the at least one grip strips have different degrees of flexibility.

14. The film dressing of claim 1, wherein a wound cushion is attached to a second side of the polymer film.

15. The film dressing of claim 1, wherein a layer promoting wound healing is applied to a second side of the polymer film.

16. The film dressing of claim 1, wherein the polymer film is selected from the group consisting of a polyurethane film, a polyester urethane film, and a polyether urethane film.

17. The film dressing of claim 1, wherein the at least one grip strip that protrudes above at least one section of the supporting film-free area protrudes to define a free gripping surface.

* * * * *